United States Patent [19]

Dumić et al.

[11] Patent Number: 5,545,659
[45] Date of Patent: Aug. 13, 1996

[54] HYDROXYLAMINES WITH HYPOGLYCEMIC ACTIVITY

[75] Inventors: Miljenko Dumić; Darko Filić, both of Zagreb; Mladen Vinković, Čakovec; Blanka Jamnicky; Mirela Eškinja, both of Zagreb, all of Croatia

[73] Assignee: PLIVA farmaceutska, kemijska, prehrambena i kozmeticka industrija, dionicko drustvo, Croatia

[21] Appl. No.: 390,955

[22] Filed: Feb. 21, 1995

[30] Foreign Application Priority Data

Feb. 21, 1994 [HR] Croatia .................... P940123A

[51] Int. Cl.$^6$ ............... A61K 31/635; C07D 491/56
[52] U.S. Cl. ...................... 514/450; 548/958
[58] Field of Search .............. 548/958; 514/450

[56] References Cited

U.S. PATENT DOCUMENTS

| | | | |
|---|---|---|---|
| 3,694,509 | 9/1972 | Rylander et al. | 260/578 |
| 3,715,397 | 2/1973 | Rylander et al. | 260/575 |
| 3,927,101 | 12/1975 | Le Leduc | 260/580 |
| 4,723,030 | 2/1988 | Davis | 560/19 |
| 5,166,435 | 11/1992 | Sharma et al. | 564/300 |
| 5,266,173 | 11/1993 | Bandlish et al. | 204/72 |
| 5,286,744 | 2/1994 | Dumic et al. | 514/450 |

FOREIGN PATENT DOCUMENTS

| | | |
|---|---|---|
| 0086363 A1 | 4/1993 | European Pat. Off. . |
| 2357370 | 5/1974 | Germany . |

OTHER PUBLICATIONS

Dumic et al, "1–Sulfonyl–1a,2,6,6a–tetrahydro, etc" Tet. Let. 34 (22) pp. 3639–3642 (1993).

*Primary Examiner*—Patricia L. Morris
*Attorney, Agent, or Firm*—Pollock, Vande Sande & Priddy

[57] ABSTRACT

Novel 1-(2-,3- or 4-hydroxylaminobenzensulfonyl-1a,2,6,6a-tetrahydro-1H,4H-[1,3]-dioxepino[5,6-b]azirines with hypoglycemic activity are prepared by selective reduction of appropriate 1-(2-,3- or 4-nitrobenzenesulfonyl) derivatives.

7 Claims, No Drawings

HYDROXYLAMINES WITH HYPOGLYCEMIC ACTIVITY

The invention relates to novel hydroxylamines, methods and intermediates for their preparation and to the use thereof.

Compounds of general formula I

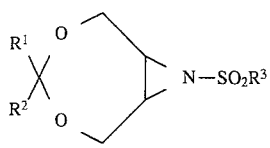

wherein $R^1$ and $R^2$ represent a hydrogen atom, a straight-chain or branched alkyl with 1–4 C atoms or phenyl, or $R^1+R^2$ together represent an alkylidene group with 4–6 C atoms, and $R^3$ represents an o-, m-, or p-hydroxyaminophenyl group, have not been known so far.

Now it has been found that these compounds have valuable pharmacological properties, especially hypoglycemic activity, irrespective of the application route that can be an intravenous, subcutaneous or oral one. Hypoglycemic activity has been determined by standard tests on warm-blooded animals, e.g. mice. For example, see U.S. Pat. No. 5,286,744, issued Feb. 15, 1994, to Dumić et. al., the entire disclosure of which is hereby incorporated by reference.

According to the process of the present invention, compounds of the general formula I can be prepared in such a way that compounds of general formula II

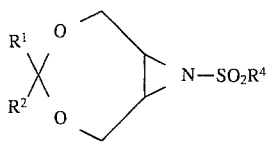

wherein $R^1$ and $R^2$ have the above-given meaning and $R^4$ represents an o-, m- or p-nitrophenyl group, are contacted with a reducing agent e.g. amalgams such as sodium amalgam, sulfide reducers such as $H_2S/NH_3/EtOH$ or $NaHS/CaCl_2$, hydrazinc reducers such as $N_2H_4 \cdot H_2O/Pd/C$, zinc reducers such as $Zn/CaCl_2$ or $Zn/NH_4Cl$, tin reducers such as $SnCl_2/^-OH$, organic reducers such as glucose or vitamin C, either electrochemically or by catalytic hydrogenation in the presence of palladium or platinum catalysts.

By catalytic hydrogenation the reduction is best performed in the presence of palladium catalysts such as $Pd/BaSO_4$ or Pd/C or platinum catalysts such as Pt/C in inert organic solvents of alcohol type such as methanol, ethanol or tert.-butanol, carboxylic acid esters such as ethyl acetate, under hydrogen pressure of 0–4 bar and at temperatures from −10° C. to +50 ° C.

Suitable starting materials of general formula II are compounds which are appropriately substituted in accordance with the definition of symbols $R^1$ and $R^2$ as given in general formula I and $R^4$ as given in general formula II. They can be easily prepared by sulfonation of the corresponding dioxepinoazirines with o-, m- and p-nitro substituted benzenesulfochlorides (M. Dumić et al., WO 93 04067 of 04.03.1993).

With regard to what has been said above, the novel hydroxylamines of the general formula I represent effective hypoglycemic agents and by conventional processes of pharmaceutical technology they can be transformed into appropriate pharmaceutical formulations such as tablets, pills, powders, granules, solutions etc. with short-term or prolonged activity for the therapy of diabetes mellitus.

The present invention is illustrated, yet in no way limited, by the following examples.

EXAMPLE 1

General process for the preparation of novel hydroxylamines of the general formula I The nitro derivative of the general formula II (0.50 g) is dissolved in an inert solvent and, after the addition of 5% Pd/C (0.05 g), it is hydrogenated for 60 minutes at the hydrogen pressure of 1 bar and at room temperature. The catalyst is filtered off by suction and the tiltrate is evaporated to dryness at reduced pressure. By recrystallization of the evaporation residue, a hydroxylamine of the general formula I is obtained.

EXAMPLE 2

In a manner analogous to the general process described in Example 1, from 0.50 g of derivative II ($R^1=R^2=H$, $R^4=NO_2-C_6H_4-$) by hydrogenation in 60 ml of ethyl acetate the compound I ($R^1=R^2=H$, $R^4=$p—HONH—$C_6H_4-$) is obtained, m.p. 145°–147° C./ethyl acetate-petroleum ether.

We claim:

1. Compound of the formula I

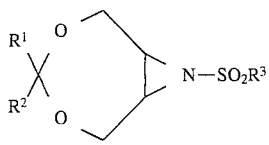

wherein $R^1$ and $R^2$ represent a hydrogen atom, a straight-chain or branched alkyl with 1–4 C atoms or phenyl, or $R^1+R^2$ together represent an alkylidene group with 4–6 atoms and $R^3$ represents an o-, m-, or p-hydroxyaminophenyl group.

2. Compound according to claim 1, wherein $R^1=R^2=H$, $R^3=$o—HOI—$C_6H_4$—.

3. Compound according to claim 1, wherein $R^1=R^2=H$, $R^3=$m—HONH—$C_6H_4$—.

4. Compound according to claim 1, wherein $R^1=R^2=H$, $R^3=$p—HONH——$C_6H_4$—.

5. Pharmaceutical composition with hypoglycemic activity, which comprises an effective amount of a hydroxyamine of the general formula I according to claim 1 as an active compound, and a pharmaceutically acceptable carrier.

6. Pharmaceutical composition with hypoglycemic-activity, which comprises an effective amount of a hydroxyamine of the general formula I according to claim 2 as an active compound.

7. Pharmaceutical composition with hypoglycemic activity, which comprises an effective amount of a hydroxyamine of the general formula I according to claim 3 as an active compound.

* * * * *